United States Patent [19]

Stevens

[11] Patent Number: 5,545,214
[45] Date of Patent: Aug. 13, 1996

[54] ENDOVASCULAR AORTIC VALVE REPLACEMENT

[75] Inventor: John H. Stevens, Palo Alto, Calif.

[73] Assignee: Heartport, Inc., Redwood City, Calif.

[21] Appl. No.: 206,419

[22] Filed: Mar. 4, 1994

Related U.S. Application Data

[62] Division of Ser. No. 730,559, Jul. 16, 1991, Pat. No. 5,370,685.

[51] Int. Cl.⁶ .................................................. A61F 2/24
[52] U.S. Cl. .......................... 623/2; 606/191; 128/898
[58] Field of Search ........................... 623/2, 11, 66; 604/94, 101; 606/159, 170, 171, 196, 191; 128/DIG. 8, 898

[56] References Cited

U.S. PATENT DOCUMENTS

| | | |
|---|---|---|
| 3,409,013 | 11/1968 | Berry . |
| 3,587,115 | 6/1971 | Shiley . |
| 3,671,979 | 6/1972 | Moulopoulos . |
| 4,056,854 | 11/1977 | Boretos et al. . |
| 4,631,052 | 12/1986 | Kensey . |
| 4,883,458 | 11/1989 | Shiber . |
| 4,966,604 | 10/1990 | Reiss . |
| 4,979,939 | 12/1990 | Shiber . |
| 5,007,896 | 4/1991 | Shiber . |
| 5,011,488 | 4/1991 | Ginsburg . |
| 5,026,366 | 6/1991 | Leckrone . |
| 5,032,128 | 7/1991 | Alonso . |
| 5,047,041 | 9/1991 | Samuels . |
| 5,080,660 | 1/1992 | Buelna . |
| 5,089,015 | 2/1992 | Ross . |
| 5,152,771 | 10/1992 | Sabbaghian et al. . |
| 5,167,628 | 12/1992 | Boyles ............................ 604/101 |
| 5,295,958 | 3/1994 | Shturman ........................... 604/96 |

FOREIGN PATENT DOCUMENTS

| | | |
|---|---|---|
| 91/17720 | 11/1991 | WIPO . |
| 92/17118 | 10/1992 | WIPO . |

OTHER PUBLICATIONS

Merck Manual of Diagnosis & Therapy 16th Edition, 1992, pp. 546–552.
A. Yamaguchi et al, "A Case of a Reoperation Using a Balloon Catheter With Blocked Pars Ascendes Aortae" Oct. 1989 Kyobu, Geka.

*Primary Examiner*—Mary Beth Jones
*Assistant Examiner*—Robert Clarke
*Attorney, Agent, or Firm*—Townsend and Towsend and Crew

[57] ABSTRACT

The subject invention relates to a valve replacement system together with methods of preparation and use, are provided for endovascular replacement of a heart valve in a host. The valve replacement system includes up to five components: (1) a prosthetic valve device, (2) a valve introducer device, (3) an intraluminal procedure device, (4) a procedure device capsule, and (5) a tissue cutter. The system provides for endovascular removal of a malfunctioning valve and subsequent replacement with a permanent prosthetic heart valve.

8 Claims, 4 Drawing Sheets

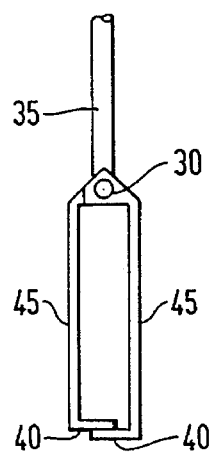
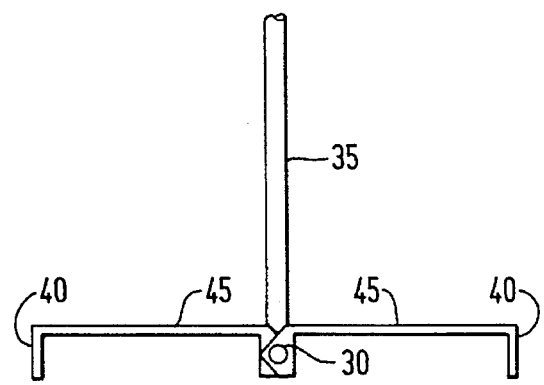
FIG. 5　　　　　FIG. 6
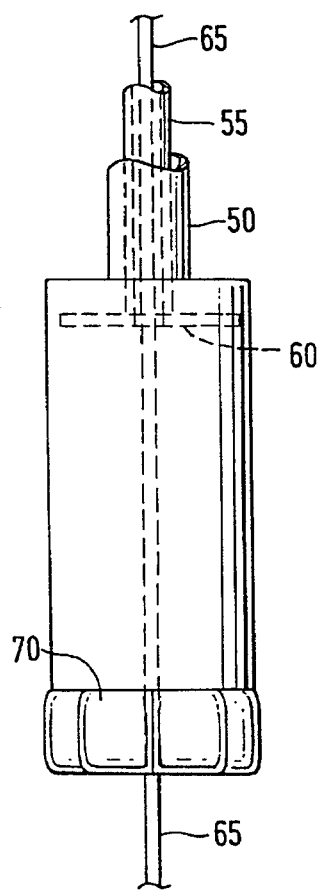
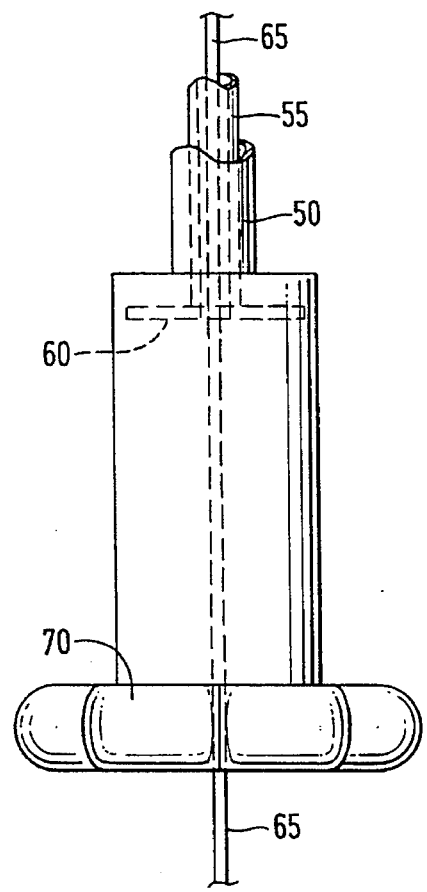
FIG. 7　　　　　FIG. 8

ENDOVASCULAR AORTIC VALVE REPLACEMENT

This is a divisional application of application Ser. No. 07/730,559, which was filed on Jul. 16, 1991, now U.S. Pat. No. 5,370,685.

INTRODUCTION

Field of the Invention

This invention relates to devices and methods for endovascular replacement of a heart valve.

Background

It is often necessary to replace malfunctioning heart valves within the body. Heart valve replacement generally has been accomplished by a major open heart surgical procedure, requiring general anesthesia, full cardiopulmonary bypass with complete cessation of cardiopulmonary activity, seven to ten days of hospitalization and months of recuperation time. The mortality rate with this type of procedure is about five to six percent.

Endovascular procedures for valve replacement provide an alternative to open heart surgery. For example, in patients with serious aortic valve disease who are too compromised to tolerate open heart surgery, surgeons have used endovascular balloon aortic valvuloplasty. This procedure involves use of endovascular balloon dilatation to split commissures in diseased aortic valves with commissural fusion and to crack calcific plaques in calcified stenotic aortic valves. This method provides only partial and temporary relief for a patient with a stenotic aortic valve. A repeat procedure within a year of the first procedure is often required.

An alternative treatment regimen is endovascular valve supplantation. In this procedure, instruments are used to insert a mechanical valve in the lumen of a central blood vessel via entry through a distal artery, for example, the brachial or femoral artery. The descriptive terms distal and proximal, when used in relation to the vasculature in this application, refer to directions further and closer from the valve replacement or procedure site, as applicable. A guide wire is placed through the entry vessel and fluoroscopically directed to the desired situs. Flexible catheters are then guided over the guide wires which are used to propel and direct the new valve through the blood vessel to the desired central location near to the malfunctioning heart valve where it supplants the function of the existing valve.

Endovascular heart procedures, in contrast to open heart surgical procedures, would require only local anesthesia, partial or no cardiac bypass, one to two days hospitalization, and should have a reduced mortality rate as compared to open heart procedures. However, as discussed in the literature but never actually practiced, endovascular heart valve supplantation is limited to supra-annular arterial based mechanical valves which require an elongated mounting catheter originating at the distal arterial entry point to maintain the position of the valve in the aorta and therefore does not provide a permanent or internalized system. Valve supplantation is also limited to treating regurgitant aortic valves and is not applicable to stenotic aortic valves or any other malfunctioning heart valves. In addition, once implanted, mechanical valves predispose the patient to thrombus formation and emboli, mandating long term anticoagulant therapy; intracranial hemorrhages are a serious side effect of long term anticoagulant therapy.

A potential alternative to a mechanical valve is a bioprosthetic valve. A bioprosthetic valve can be either a homograft (a fresh human), allograft (a fixed human) or a xenograft (a fixed other species) valve. Homograft valves, in contrast to xenograft valves, are rarely used because of the lack of access to fresh human valves. Porcine glutaraldehyde preserved valves are often used since they are readily accessible and storable and are available in a variety of sizes. Bioprosthetic valve replacement does not predispose a patient to thrombus formation or emboli, and, therefore, requires no long-term anticoagulant therapy. Bioprosthetic valves are presently a mainstay in aortic valve replacement. Bioprosthetic heart valve replacement is preferable in patients who cannot tolerate long-term anticoagulant therapy or are otherwise potentially noncompliant with a long-term medical regime.

To date, bioprosthetic and mechanical valves have been inserted near or at the native annulus site through open heart surgery and except for the Magovern-Cromie Valve which used pins to fix the valves have required sutures for fixation at the insertion site; means for endovascular valve replacement with any valve are not available. It would therefore be of interest to provide a endovascular means i) to easily remove a dysfunctional natural or prosthetic valve and ii) to replace the dysfunctional valve with a endovascularly replaceable bioprosthetic or flexible synthetic valve, independently fixed without sutures or catheter, near or at the native valve annulus site.

Relevant Literature

U.S. Pat. No. 3,671,979 to Moulopoulos, issued Jun. 27, 1972, describes a endovascularly inserted conical shaped umbrella-like valve positioned and held in place by an elongated mounting catheter at a supra-annular site to the aortic valve in a nearby arterial vessel. The conical end points toward the malfunctioning aortic valve and the umbrella's distal ends open up against the aorta wall with reverse blood flow, thereby preventing regurgitation.

U.S. Pat. No. 4,056,854 to Boretos, issued Nov. 8, 1977, describes a endovascularly inserted, catheter mounted, supra-annular valve in which the circular frame abuts the wall of the artery and attached flaps of flexible membrane extend distally in the vasculature. The flaps lie against the artery wall during forward flow, and close inward towards the central catheter to prevent regurgitation during reverse blood flow. The Boretos valve was designed to be positioned against the artery wall during forward flow, as compared to the mid-center position of the Moulopoulos valve, to reduce the stagnation of blood flow and consequent thrombus and embolic formation expected from a valve at mid-center position.

Reviews relating to replacement valves include: *Gibbon's Surgery of the Chest*, 5th Ed., David C. Sabiston, Jr., M.D., Frank D. Spencer, M.D., 1990, Vol. II, Ch. 52, pp. 1566–1596, and *Textbook of Interventional Cardiology*, Eric J. Topol, 1990, Chs. 43–44, pp. 831–867.

SUMMARY OF THE INVENTION

According to the subject invention, a valve replacement system together with methods of preparation and use, are provided for endovascular replacement of a heart valve in a host. The valve replacement system includes up to five components: (1) a prosthetic valve device, (2) a valve introducer device, (3) an intraluminal procedure device, (4) a procedure device capsule, and (5) a tissue cutter. The system provides for endovascular removal of a malfunctioning valve and subsequent replacement with a permanent prosthetic heart valve.

DESCRIPTION OF THE DRAWINGS

FIG. 5 illustrates a tissue cutter in a closed position.

FIG. 6 illustrates a tissue cutter in an open position.

FIG. 7 illustrates a side view of a valve introducer capsule with bracer balloons deflated.

FIG. 8 illustrates a side view of a valve introducer capsule with bracer balloons inflated.

DESCRIPTION OF THE SPECIFIC EMBODIMENTS

The present invention relates to the (supplantation or) replacement of a cardiac valve in a host through endovascular means. The valve replacement system includes up to five components: (1) a prosthetic valve device, (2) an valve introducer device, (3) an intraluminal procedure device, (4) a procedure device capsule, and (5) a tissue cutter. All the components of the system are not required to be used in conjunction with valve replacement; the description of valve replacement using all the components is merely exemplary.

Figure 1:
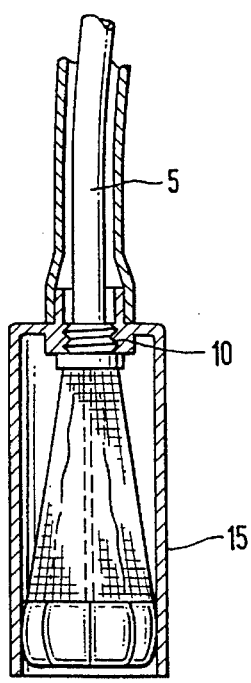
FIG. 1 illustrates a procedure device capsule side view.
Figure 2:
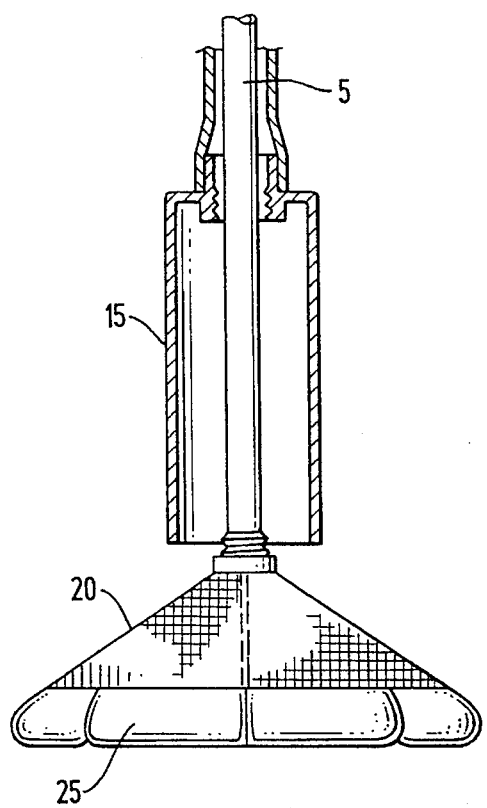
FIG. 2 illustrates a side view of an intraluminal procedure device.
Figure 4:
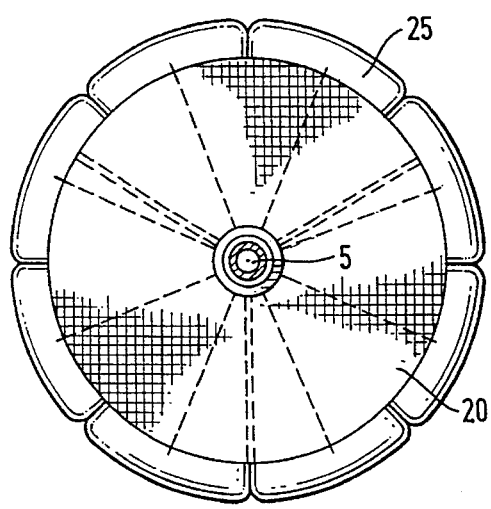
FIG. 4 illustrates a top view of an intraluminal procedure device.
Figure 3:
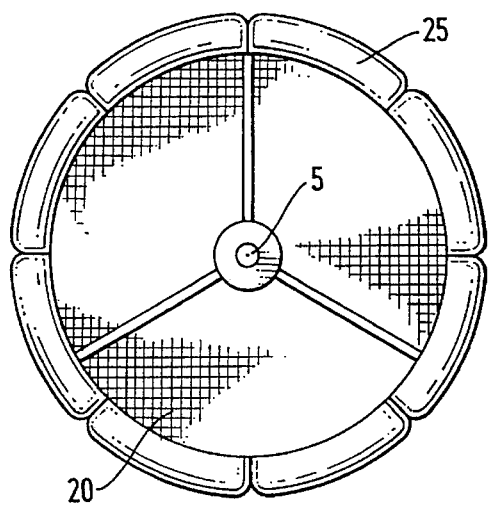
FIG. 3 illustrates a bottom view of an intraluminal procedure device.

In a general method, the procedure device capsule (FIG. 1), which contains the intraluminal procedure device, is inserted into an entry point in the host and used to transport the intraluminal device to the desired situs, over a guide wire. At the situs, a selectively permeable barrier of the intraluminal procedure device exits from the procedure device capsule, expands in a controlled and adjustable manner and abuts the lumen of the vessel encircling the old valve or prosthesis (FIGS. 2, 3 & 4). The guide wire is withdrawn from the working channel of the intraluminal procedure device leaving the channel available for the passage of the tissue cutter, angioscope, ultrasound, tissue graspers, and tissue cutting devices. The channel can also be used for irrigation or applied to suction apparatus to remove debride, thrombus or other material.

The tissue cutter then is inserted into the host through the working channel of the intraluminal procedure device to the valve situs where it is used to cut and remove the existing valve from the situs (FIGS. 5,6). Accurate positioning of the cutter is assured using transesophageal echocardiography and intra-arterial or intra-cardiac ultrasound and angioscopy. The precision of the valve extraction and replacement is important to the success of endovascular valve replacement. There are several imaging techniques presently available providing complementary options to assure this precision: 1) Transesophageal echocardiography can be continuously used; 2) Intravascular ultrasound passed through the working channel of the intraluminal procedure device; 3) Intravascular ultrasound passed intravascularly via the venous system through the intra-atrial septum across the mitral valve and into the left ventricle; 4) An angioscope can be passed into the left ventricle in a like manner which would provide the added benefit of allowing constant high definition imaging of the entire procedure and high flow irrigation.

Any tissue debris resulting from the procedure is trapped by the barrier of the intraluminal procedure device or is removed from the host through suction and tissue retrieval devices inserted via the working channel of the intraluminal procedure device. Tissue debris is removed via the working channel of the intraluminal procedure device with suction, grasping devices (e.g. dormier basket or grasping forceps) or is caught in the barrier of the intraluminal procedure device to avoid embolism. Once all the necessary tissue has been removed, contraction of the tissue cutter allows for removal of the tissue cutter through the working channel of the intraluminal procedure device. The barrier of the intraluminal procedure device is contracted and the intraluminal procedure device is withdrawn into the procedure device capsule which is then removed.

Figure 9:
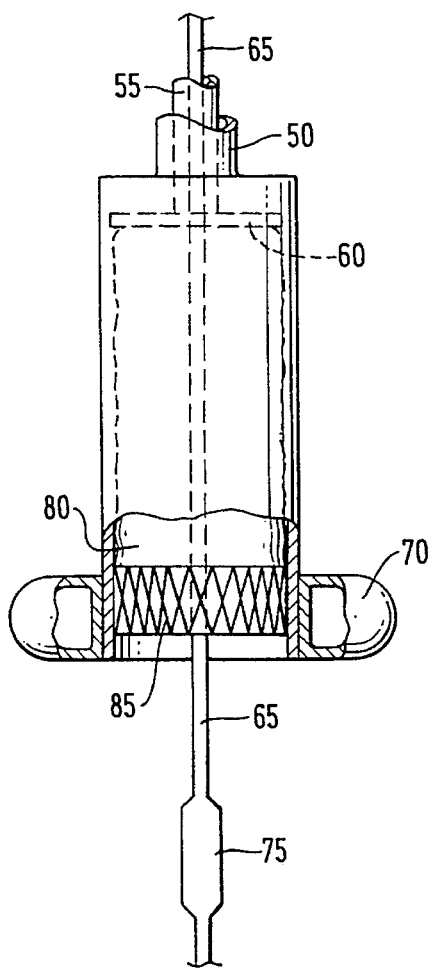
FIG. 9 illustrates a side view of a valve introducer capsule with balloons passed over a guide wire.

The valve introducer device containing the prosthetic valve device is then inserted and used to transport the replacement valve to the valve situs, over a guide wire (FIG. 7). The bracer of the valve introducer device, which optionally can include positioning balloons surrounding the introducer capsule of the valve introducer device, inflates in a differential manner, such that certain balloons inflate more or less than others, to assure accurate positioning of the prosthetic valve when delivered out of the introducer capsule (FIG. 8). A means for pushing the valve out of the introducer capsule, after the introducer capsule is in the appropriate position, is to advance the pusher device of the valve introducer device within the capsule (FIG. 9). A means for securing the mounting pins into the desired situs is to inflate a balloon inside of the prosthetic valve device and within the lumen of the mounting ring (FIGS. 10–15). The capsule positioning balloons and the intraluminal balloon can then be deflated and the valve introducer device is withdrawn.

In order to support the circulation of the patient during the endovascular aortic valve replacement it will be necessary to place the patient on partial or complete cardiopulmonary bypass. There are presently available several means to provide this support. For example, one method is percutaneous insertion of venous and arterial cannula with decompression of the left ventricle by insertion of a pulmonary arterial line allowing aspiration of blood and marked diminution of left ventricular filling and ejection.

The invention provides several advantages, including the ability to replace or supplant existing cardiac or other valves or prostheses via a sutureless endovascular means avoiding the riskier, more expensive and complicated open heart surgical procedure. This prosthetic valve device, preferably using a bioprosthesis or other thrombus resistant flexible prosthesis for the valve leaflets, will avoid the need for permanent anti-coagulant therapy for the host. Once inserted, the valve is capable of operating autonomously. Further, bioprosthesis replacement valves in the past have required sutures and, therefore, open heart surgery for fixation at the annulus or vasculature situs. The mounting device used with the valve of the subject invention allows the invention to be fixed via endovascular means without the need for sutures. The prosthetic valve device is inserted on a permanent basis, and remains for the life of the valve incorporated in the device. The life of a bioprosthetic valve, for example, can extend to over twenty years. Future developments can provide alternative prosthetic valves with a markedly extended life. Since most of the patients who are unable to tolerate open heart procedures are elderly, the bioprosthetic valve will usually outlive the patient. The intraluminal procedure device and the cutter allow for the novel ability to perform endovascular procedures without the serious side effect of causing loose debris and other emboli to circulate within the vasculature.

The components of the valve replacement system will now be described. The procedure device capsule comprises a cylindrical sleeve made of flexible durable material, for example, teflon coated polyurethane or other materials which have the following characteristics: flexible such that it can be maneuvered easily through vasculature, durable such that it can withstand the abrasive contact and pressure of instruments inserted and contained within it, and non-thrombogenic such that blood clots do not develop and adhere to its surface. The procedure device capsule has a generally cylindrical outside surface and a generally cylindrical inside surface with a mesh or grid design. It is characterized as capable of containing the barrier of the intraluminal procedure device and other devices which could be used intraluminally, and of intraluminal transport. The device is introduced over a guide wire to the valve situs (FIG. 1).

A means for withdrawing the procedure device capsule (15) partially to allow for full expansion of the intraluminal procedure device is to have the distal end of the procedure device capsule and the proximal end of the working channel (5) of the intraluminal procedure device threaded together by a screw mechanism (10). Upon rotation of the working channel on the threads of the procedure device capsule, the intraluminal procedure device can be advanced within and out of the procedure device capsule. After completion of work, the intraluminal procedure device can be drawn back into the procedure device capsule and then secured within the procedure device capsule and then secured within the capsule by rotating the working channel on the threads of the procedure device capsule in the reverse direction (FIG. 2).

The intraluminal procedure device functions to aid the performance of intraluminal procedures via endovascular or other intraluminal means and comprises a layer (the "barrier") and a tube (the "working channel"). The barrier (20) comprises an umbrella-like cone with a generally conical outside surface and a generally conical inside surface (FIG. 2). Materials for fabrication of the cone include flexible, durable, and selectively permeable (such that only certain selected sizes of particles may pass through it) material, for example, polypropylene, polyester, dacron or nylon mesh over supports of stainless steel. The apex of the cone is perforate to allow an exit from the working channel and points downstream in the vasculature. The barrier is suspended over the stainless steel tripod (FIG. 3). Attached circumferentially to the barrier is an expansion device (25, the "Bracer"), such as a balloon (FIG. 4). The balloon can have four to twenty segments, each separated by a diaphragm. Each balloon segment has a separate inflation, deflation channel which allows each segment to have differential inflation directed from a central external control.

The external device for inflation and/or deflation of each segment of the Bracer is comprised of means such as syringes or compressed air cylinders in parallel. Each has a valve in series allowing inflation when pressure is applied and passive or active deflation when open. Differential inflation of each balloon segment allows subtle changes in the angle of the working channel in relation to the valve situs. Once inflated the barrier is characterized as capable of allowing blood flow through its permeable surface preventing back pressure and embolization, and providing a working procedure region bounded by the inner surface of the barrier and extending from the barrier's distal ends proximally into the vasculature and heart (FIG. 2).

The tube of the intraluminal procedure device, the working channel, comprises an elongated flexible cylinder. The working channel is made of durable flexible material, for example, teflon coated polyurethane or other materials which have the following characteristics, flexible, durable, and non-thrombogenic. The tube has a generally cylindrical outside surface and a generally cylindrical inside surface. The proximal open end of the working channel is attached around the barrier's perforated conical apex and its distal end extends out and through the vascular entry point. For use in an adult human, the working channel preferably has an internal diameter of about 0.5 to 10 millimeters making it capable of providing passage for instruments, for example, ultrasound, angioscopy, debridement, suction, irrigation, retrieval devices, and the tissue cutter, from outside the host to the working procedure region. For use in a host other than an adult human, this internal diameter size range can be varied up or down depending on the size of the host and lumen. It can also be useful to have suction or irrigation applied to the working channel.

The tissue cutter comprises at least one proximal blade and a cable. The proximal blade (45) comprises a collapsible hinged (30) blade of length varying from about 1.0 to 20 millimeters with sharp cutting surfaces. This range of blade length can vary up or down depending on the size of host and lumen. Alternatively, the proximal blade can comprise a flexible wire capable of high speed rotation which would deliver a cutting contact to the tissue. The blade is made of rigid durable material, for example, stainless steel or elgiloy. The proximal blade is characterized as capable of passage through the working channel to the working procedure region in an unextended state, and then of extension of itself to allow for cutting of any undesired tissue and finally of return to its unextended state. Additional blades can be attached to the proximal blade to increase the cutting ability of the tissue cutter (FIGS. 5,6). For example, two shorter approximately 0.5 to 5.0 millimeter distal blades (40) can be attached through melding, hinging, or other connecting methods, to the distal ends of the proximal blade. This blade length range can vary up or down in size depending on the size of host and lumen. These blades provide sharp cutting surfaces at a range from about thirty to one hundred and fifty degree angles to the proximal blade which allows for simultaneous cutting at various angles.

The cable (35) of the tissue cutter comprises a flexible durable elongated wire and is characterized as being capable of powering the tissue cutter (FIG. 6). The cable is attached to the proximal blade at a central or off-center position and connected distally to an external motor. For example, the cable can be a steel coaxial cable connected to a DC motor for variable speed rotation.

The valve introducer device comprises a layer, a tube, a pusher device and a bracer. The layer of the valve introducer device, the introducer capsule, comprises a cylindrical sleeve having a generally cylindrical outside surface and a generally cylindrical inside surface reinforced at the proximal end which is open, and having a semi-closed distal end with a perforate opening, the distal opening, having a diameter approximately the same as the internal diameter of the introducer channel (50) (FIG. 7). The introducer capsule is made of durable, non-thrombogenic, flexible material, for example, teflon coated polyurethane with a grid or mesh design. The introducer capsule is characterized as being capable of containing and maintaining the prosthetic valve device in its compressed state allowing for easy transport through the host's vasculature. The introducer capsule is reinforced at its base with a solid rather than mesh or grid, for example, solid polyurethane coated with teflon to support the mounting ring and the mounting pins of the prosthetic valve device in its compressed state while within the introducer capsule.

The bracer (70) is circumferentially attached to the external surface of the introducer capsule at the capsule's proximal end. The bracer comprises a differentially expandable device, such as a series of segmented balloons, and is characterized as having the capability of expanding to hold the introducer capsule in a precise position during delivery of the prosthetic valve device (FIG. 8). Each segmented balloon can have an inflation/deflation channel to provide autonomous segmental expansion and compression. Differential expansion of the series of segmented balloons is directed from a central external control as done with the intraluminal procedure devices. Inflation of each differentially allows accurate positioning of the introducer capsule in proximity to the desired site of valve placement.

The tube of the valve introducer device, the introducer channel, comprises an elongated flexible cylinder. The introducer channel (50) is made of durable, flexible material, for example, teflon coated polyurethane or other materials which have the following characteristics: flexible, durable, and non-thrombogenic. The introducer channel has a generally cylindrical outside surface and a generally cylindrical inside surface. The proximal end of the introducer channel is attached circumferentially around the distal opening of the introducer capsule and the introducer channel's distal end exits through the vascular entry point (FIG. 9). For use in an adult human, the introducer channel preferably has an internal diameter of about 0.5–10 mm, making it capable of containing the pusher channel (55) of the pusher device. For use in a host other than an adult human, this internal diameter size range can be varied up or down depending on the size of the host and lumen. The introducer channel and pusher channel are also characterized as being capable of allowing suction or irrigation instruments within its lumen.

The pusher device comprises a disc and a tube. The pusher disc (60) of the pusher device, the pusher disc, comprises a generally circular disc, with a generally flat distal surface, a generally flat proximal surface and a central opening. The diameter of the opening should be smaller than the diameter used in the introducer channel. The pusher disc is made of a durable, flexible material such as teflon coated polyurethane or other materials which have the following characteristics: flexible and durable. The proximal surface of the pusher disc abuts the prosthetic valve device contained within the introducer capsule (FIG. 9).

Figure 10:
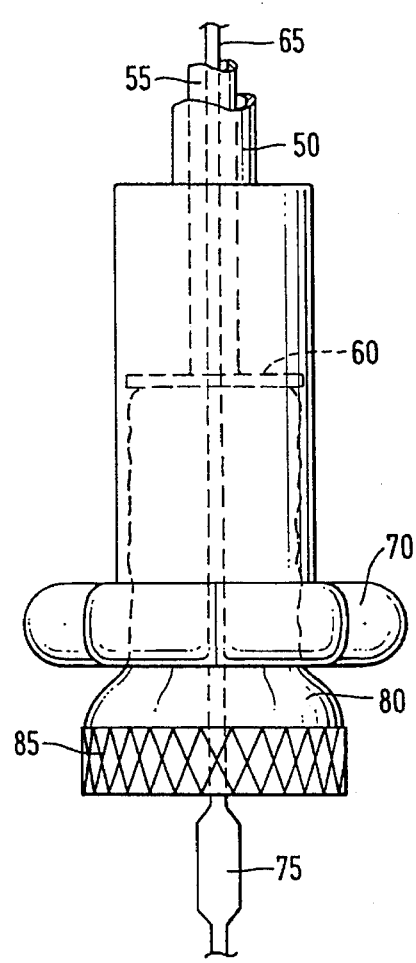
FIG. 10 illustrates a side view of a pusher disc advancing a valve out of the introducer capsule.

Attached at the pusher disc's distal surface circumferentially around the central opening of the pusher disc is the proximal end of the tube, the pusher channel. The pusher channel, comprises an elongated flexible cylinder and is made of durable, flexible, non-thrombogenic material, that can maintain its structural integrity such that it will not distort upon application of external pressure (e.g. teflon coated polyurethane). The pusher channel has a generally cylindrical outside surface and a generally cylindrical inside surface and has a smaller internal diameter than that used in the introducer channel (FIG. 10). It is characterized as capable of being contained within the lumen of the introducer channel with its distal end extending beyond the vascular entry point via the introducer channel and of allowing passage of the mounting balloon (75) and guide wire (65). It is also characterized as being capable of advancing within the lumen of the introducer channel, upon application of external pressure at the vascular entry point to advance the pusher disc within the introducer capsule. The pusher channel is also characterized as being capable of allowing suction or irrigation instruments within its lumen.

Figure 11:
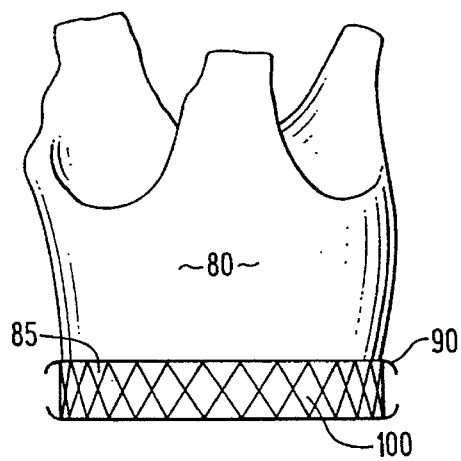
FIG. 11 illustrates an aortic valve in the side position.
Figure 12:
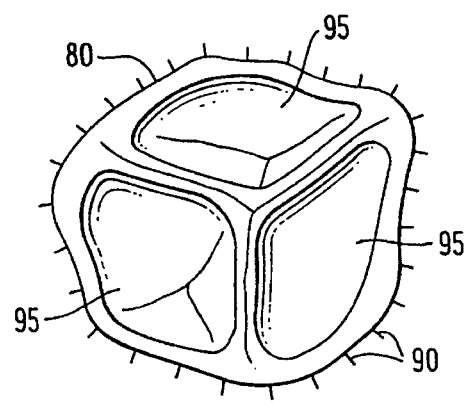
FIG. 12 illustrates an aortic valve from the top view.

The prosthetic valve device comprises a sleeve (80), a valve and an annulus. The sleeve is a flexible cylindrical shaped cylinder having a generally cylindrical outside surface and a generally cylindrical inside surface. The sleeve is secured on its inside surface to the valve and on the base of its outside surface to a compressible annulus, the mounting ring (85) (FIGS. 11, 12). Securing means can include suturing, chemical bonding, laser welding, stapling, or other methods. Securing materials can include polypropylene, polyester, nylon, stainless steel or other inert, durable materials. The sleeve is of durable, host compatible, non-thrombogenic, flexible and compressible material, for example, dacron or polytetrafluoroethylene, to allow it to be easily compressed, maneuvered and transported through the vasculature to permit endovascular placement. The sleeve's durability permits secure attachment to other objects and layers, and allows the sleeve to remain intact despite the replacement procedure, and the long term of the prosthetic device within the host. All components of the prosthetic valve device, the mounting ring, sleeve and valve, are flexible, compressible, non-thrombogenic and durable.

Secured to the inner layer of the prosthetic valve device comprises a valve which functions to permit unidirectional circulatory flow of blood. The valve comprises a cylindrical shaped annulus (100) having a generally cylindrical outside surface and a generally cylindrical inside surface containing at least one cusp (95) to permit blood flow in a single direction. The cusp(s) are attached at the distal end (relative to blood flow) of the cylindrical annulus. The cusp(s) open distally to permit the circulation's flow of blood through the valve situs, and then alternately close centrally to prevent circulation back-flow. The valve is flexible, compressible, host-compatible, and non-thrombogenic. The valve can be, for example, a glutaraldehyde fixed porcine aortic valve which has three cusps that open distally to permit unidirectional blood flow. The valve can also be fresh, cryopreserved or glutaraldehyde fixed allografts or xenografts. The optimal material will be synthetic such that it is manufactured from non-biological materials, non-thrombogenic, flexible such that it can be transported through the vasculature, biocompatible and very durable such that it can withstand a permanent fixation at the valve site. It is highly desirable to use flexible material where the valve is to be inserted via endovascular means.

Figure 13A:
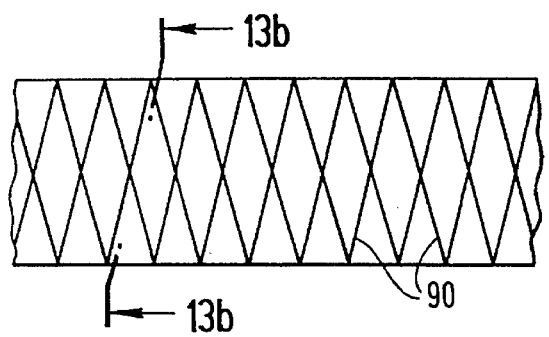
FIG. 13 illustrates a side view of an aortic valve with the mounting ring in the closed position.
Figure 13B:
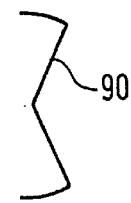
Figure 14A:
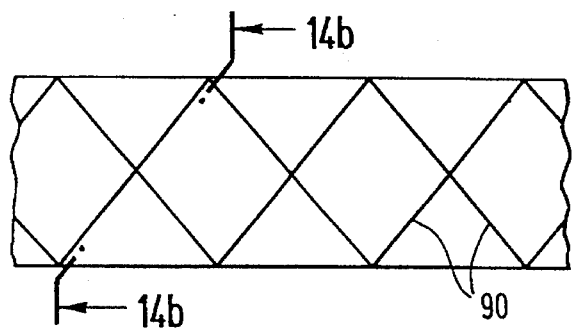
FIG. 14 illustrates a front view of an aortic valve with the mounting ring in the open position.
Figure 14B:
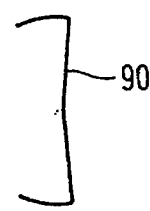
Figure 15A:
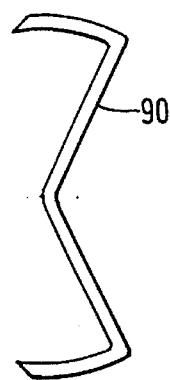
FIG. 15 is a graphic illustration of a side view of a mounting pin confirmation change with balloon inflation.
Figure 15B:
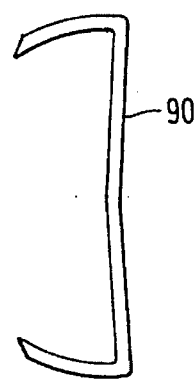

The mounting ring (85) of the prosthetic valve device is preferably attached at the base of the outside surface of the sleeve. The mounting ring is made of materials that are durable, have been high tensile strength, excellent fatigue characteristics and corrosion resistant (for example, stainless steel, MP35N or elgiloy) and is structured in a compressible architecture such that it can contract upon application and expand upon release of external pressure and still maintain its basic formation. The mounting ring has a generally cylindrical outside surface and a generally cylindrical inside surface comprised of a series of mounting pins (90) to fix the prosthetic valve device at the designated valve situs (FIGS. 13–15). The mounting ring provides endovascular sutureless fixation of the device allowing it to operate autonomously. The pins are secured by melding, welding or other connecting methods, at about 30 to about 150 degree angles to the mounting ring. The composite of angles provides for secure fixation such that the prosthetic valve device can tolerate the degree and directional pressure variations on the valve occurring during the different phases of the cardiac cycle. As uniform pressure is exerted at the inner surface of the mounting ring, as for example by inflation of the mounting balloon, the mounting ring expands and the pins extend into and secure to the lumen wall.

Once the endovascular implantation of the prosthetic valve device is completed in the host, the function of the prosthetic valve device can be monitored by the same methods as used to monitor valve replacements done by open heart surgery. Routine physical examination, periodic echocardiography or angiography can be performed. In contrast to open heart surgery, however, the host requires a short recovery period and can return home within one day of the endovascular procedure. The prosthetic valve device can be used in any patient where bioprosthetic valves are indicated, namely elderly patients with cardiac valve diseases, and patients unable to tolerate open heart procedures or life-long anticoagulation. In addition, with the development of longer-life, flexible, non-thrombogenic synthetic valve alternatives to bioprosthesis', the prosthetic valve device will be indicated in all patients where the relative advantages of the life-span, the non-thrombogenic quality, and the ease of insertion of prosthetic valve devices outweigh the disadvantages of mechanical valves. Anticoagulation may be beneficial in certain clinical situations for either short or long term use.

The intraluminal procedure device, the procedure device capsule and the tissue cutter can be independently applied, or applied in conjunction with each other, to instrumentation at or removal of cardiac, aortic, cerebrovascular, mesenteric, renal, or peripheral vessel valves or tissue, and would be especially important anywhere in the cardiac or vascular system where peripheral embolization is problematic or accurate positioning of instruments is essential. They can also be used in other body lumens, for example, the gastrointestinal, genitourinary, biliary, and respiratory tracts. In addition, the valve replacement system can be used to supplant as well as replace a host's valve or prosthesis. In that procedure the dysfunctional valve or prosthesis is not removed by the tissue cutter, and the prosthetic valve device is fixated at a vascular situs such that the device supplants the function of the dysfunctional valve or prosthesis. Also, the valve replacement system could be used in non-human species, for example, other mammals.

All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for the endovascular delivery of a replacement heart valve to an implantation site, comprising:

a) advancing though the patient's arterial system an elongated delivery catheter having proximal and distal ends, at least one inner lumen extending therein and expandable means on the distal end thereof until the distal end of the delivery catheter is near the implantation site;

b) expanding the expandable means provided on the distal end of the delivery catheter to position the distal end thereof within the patient's aorta downstream from the implantation site; and c) delivering a replacement heart valve to the implantation site through the delivery catheter.

2. The method of claim 1 including securing the replacement heart valve at the implantation site.

3. The method of claim 1 wherein the expandable means on the distal end of the delivery catheter blocks the flow of blood through the aorta when expanded.

4. A method for replacing a cardiac valve endovascularly within a host's vasculature which method comprises:

transporting an intraluminal procedure device in a procedure device capsule endovascularly through the host's vasculature, to a valve situs whereby a barrier of said intraluminal procedure device exits from said procedure device capsule, expands in a controlled and adjustable manner, abuts the lumen of the vessel, and encircles the valve situs;

advancing a tissue cutter through a working channel of said intraluminal procedure device to said valve situs, removing said cardiac valve wherein any resulting loose matter is trapped by said barrier;

contracting said barrier, withdrawing said intraluminal procedure device into said procedure device capsule, removing said procedure device capsule, and endovascularly transporting a prosthetic valve to said valve situs by means of a valve introducer device;

expanding a bracer on said valve introducer device to position said valve introducer device correctly for insertion of said prosthetic valve device at said valve situs, expelling said prosthetic valve device from said valve introducer device and inflating a balloon of said valve introducer device at the valve situs to securely mount said prosthetic valve device at said valve situs; and contacting said bracer, deflating said balloon, and removing said valve introducer device and said balloon from said host's vasculature.

5. A method for performing a therapeutic procedure on a patient's heart having an ascending aorta leading from an aortic valve which is in fluid communication with a ventricular chamber within a left portion of the patient's heart, comprising:

a) introducing into a peripheral artery of a patient a delivery catheter having proximal and distal ends, a first inner lumen extending within the delivery catheter to a port in a distal end thereof, and expandable means on the distal end proximal to the port configured to occlude a passageway within the ascending aorta;

b) advancing the delivery catheter through the patient's arterial system until the expandable means on the distal end of the catheter is disposed between the patient's ascending aorta between coronary ostia and an ostium of the patient's brachiocephalic artery;

c) expanding the expandable means on the distal end of the delivery catheter within the ascending aorta between the coronary ostia and the ostium of the brachiocephalic artery to occlude the passageway therein;

d) placing the patient on cardiopulmonary bypass; and e) after the patient is on cardiopulmonary bypass, advancing elongated means to perform a procedure on the patient's heart disposed within the inner lumen of the delivery catheter out the port in the distal end of the delivery catheter distally of the expandable member while the expandable member is occluding said passageway between the coronary ostia and the ostium of the brachiocephalic artery.

6. The method of claim 5 wherein a tissue cutter is advanced through the inner lumen of the delivery catheter and out the port in the distal end of the delivery catheter to sever at least part of the aortic valve from supporting tissue.

7. The method of claim 6 wherein the tissue cutter has at least one collapsible cutting blade and a drive shaft to rotate the cutting blade to sever at least part of the aortic valve from supporting tissue.

8. The method of claim 6 including advancing a replacement aortic valve through the inner lumen of the delivery catheter and securing the replacement aortic valve within the ascending aorta.

\* \* \* \* \*